United States Patent [19]

Ozaki et al.

[11] Patent Number: 4,497,815
[45] Date of Patent: Feb. 5, 1985

[54] 1-(N-SUBSTITUTED CARBAMOYL)-5-FLUOROURACIL DERIVATIVES AND THE CARCINOSTATIC AGENTS CONTAINING SAME AS ACTIVE INGREDIENTS

[75] Inventors: Shoichiro Ozaki, 60-397, Takahama-cho 1-chome, Matsuyama, Ehime-ken, Japan; Tomonori Hoshiko, Matsuyama; Tomio Ogasawara, Iyo, both of Japan

[73] Assignee: Shoichiro Ozaki, Matsuyama, Japan

[21] Appl. No.: 455,863

[22] Filed: Jan. 5, 1983

[51] Int. Cl.³ .................. A61K 31/505; C07D 239/55
[52] U.S. Cl. ..................... 517/274; 544/311
[58] Field of Search .................. 544/311; 424/251

[56] References Cited

U.S. PATENT DOCUMENTS 4,032,524  6/1977  Ozaki et al. ............ 544/311
4,349,552  9/1982  Takaya et al. ........... 544/311

FOREIGN PATENT DOCUMENTS 53-059680  5/1978  Japan ................... 544/311
53-130679  11/1978 Japan ................... 544/311

OTHER PUBLICATIONS

Chemical Abstracts, Ozaki et al., 90:6415u and 6416v, 1979.

Primary Examiner—Paul M. Coughlan, Jr.
Attorney, Agent, or Firm—Fisher, Christen & Sabol

[57] ABSTRACT

A 1-(N-substituted carbamoyl)-5-fluorouracil derivative represented by the following general formula:

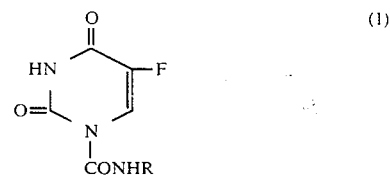

R is a 4-alkoxycyclohexyl group-containing radical which is 2,3,4-trimethoxycyclohexcylethyl, 2,3,4-trimethoxycyclohexyl, 2,4-dimethoxycyclohexylmethyl, 3,4-dimethoxycyclohexylethyl, 2,4-dimethoxycyclohexyl, 2,4,5-trimethoxycyclohexyl, 3,4-dimethoxycyclohexylmethyl, 3,4,5-trimethoxycyclohexyl, 4-ethoxycyclohexyl or 4-ethoxycyclohexylmethyl. The compounds are carcinostatic agents. The compounds are used in a therapeutically effective amount in the presence of a carrier.

12 Claims, No Drawings

1-(N-SUBSTITUTED CARBAMOYL)-5-FLUOROURACIL DERIVATIVES AND THE CARCINOSTATIC AGENTS CONTAINING SAME AS ACTIVE INGREDIENTS

TECHNICAL FIELD

This invention relates to novel 1-(N-substituted carbamoyl)-5-fluorouracil derivatives having excellent carcinostatic activity and the carcinostatic agents containing them as the main components.

BACKGROUND ART

Investigations of 1-(N-substituted carbamoyl)-5-fluorouracil derivatives have been made, because there are many carcinostatically active compounds among them. 1-[N-(monoalkyl substituted cyclohexyl) carbamoyl]-5-fluorouracil, 1-[N-(dialkyl substituted cyclohexyl) carbamoyl]-5-fluorouracil, 1-[N-(monomethoxy substituted cyclohexyl) carbamoyl]-5-fluorouracil and others were indicated in Japanese Patent Application Disclosure No. 56678/'78, 1-[N-(cyclohexylmethyl) carbamoyl]-5-fluorouracil, 1-[N-(methyl substituted cyclohexylmethyl) carbamoyl]-5-fluorouracil, 1-[N-(p-methoxy substituted cyclohexylmethyl) carbamoyl]-5-fluorouracil and others were indicated in Japanese Patent Application Disclosure No. 56679/'78, 1-(N-benzyl carbamoyl)-5-fluorouracil, 1-[N-(p-fluoro substituted benzyl) carbamoyl]-5-fluorouracil, 1-[N-(p-methoxy substituted benzyl) carbamoyl]-5-fluorouracil, 1-(N-phenetyl-carbamoyl)-5-fluorouracil and others were indicated in Japanese Patent Application Disclosure No. 59680/'78, 1-[N-(1-methyl-3-phenylpropyl) carbamoyl]-5-fluorouracil, 1-[N-(3-phenylpropyl) carbamoyl]-5-fluorouracil, 1-[N-{2-(4-methylphenyl) propyl} carbamoyl]-5-fluorouracil and others were indicated in Japanese Patent Application Disclosure No. 136267/'80, and various 1-(N-heterocyclic group substituted carbamoyl)-5-fluorouracil and the derivatives of them, 1-[N-heterocyclic group substituted alkyl) carbamoyl]-5-fluorouracil and the derivatives of them were indicated in Japanese Patent Application Disclosure No. 63966/'81. Among these known 1-(N-carbamoyl)-5-fluorouracil derivatives, 1-(N-hexyl-carbamoyl)-5-fluorouracil has been put to practical use, but investigations of the others are still insufficient.

DISCLOSURE OF THE INVENTION

The first object of this invention is to provide novel 1-(N-substituted carbamoyl)-5-fluorouracil derivatives.

The second object of this invention is to provide novel carcinostatic agents having excellent carcinostatic activity.

The above-mentioned objects of this invention can be attained by providing 1-(N-substituted carbamoyl)-5-fluorouracil derivatives represented by the following general formula as novel compounds:

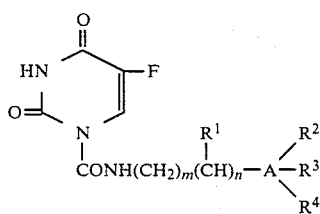

(1)

(wherein $R^1$ represents an alkyl group with 1 to 6 carbon atoms; A represents a saturated or an unsaturated ring of 3 to 7 carbon atoms; each of $R^2$, $R^3$ and $R^4$ independently represents a hydrogen or halogen atom or such a group as alkoxy with 1 to 6 carbon atoms, alkyl with 1 to 6 carbon atoms, alkylthio with 1 to 6 carbon atoms, alkoxycarbonyl with 1 to 6 carbon atoms, carboxyl, carboxyamido, sulfonic acid, sulfonamido, acylamino, sulfonylamino, alkylsulfonyl with 1 to 6 carbon atoms, nitril, nitro, acyloxy, phenyl or methylenedioxy; each of m and n represents an integral number of 0 to 4.) and by providing carcinostatic agents containing some of these compounds as the active constituents.

FURTHER DESCRIPTION OF THE INVENTION AND THE BEST MODE OF CARRYING OUT THE INVENTION

In general formula (1) representing the compounds of this investigation, A represents such a saturated or an unsaturated ring of 3 to 7 carbon atoms as cyclopropyl, cyclopentyl, cyclohexyl, cyclohexenyl, phenyl, cycloheptyl or cycloheptenyl.

The 1-(N-substituted carbamoyl)-5-fluorouracil derivatives of this invention can be obtained by one of the following two methods.

The first is the method by which 5-fluorouracil is made to react with the isocyanates represented by the following general formula:

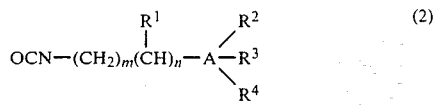

(2)

and the second is the method by which 1-chlorocarbonyl-5-fluorouracil is made to react with any of the amines represented by the following general formula:

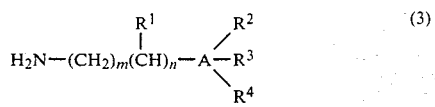

(3)

In general formulae (2) and (3), $R^1$, A, $R^2$, $R^3$, $R^4$, m and n are the same as those in general formula (1), respectively.

5-Fluorouracil can be allowed to react with isocyanate usually by dissolving or suspending 5-fluorouracil in organic solvent and adding isocyanate to it. Sometimes, isocyanate is synthesized by decomposing carboxylic acid azide and it is allowed to react with 5-fluorouracil without being isolated. Pyridine and dimethylacetamide, etc., are suitable solvents to be used in this reaction. The reaction temperature is room temperature—110° C. and the reaction period is 1 to 10 hr.

In the reaction of 1-chlorocarbonyl-5-fluorouracil and amine, 5-fluorouracil is dissolved in a suitable solvent in the first place and the solution is treated with phosgene at a low temperature to synthesize 1-chlorocarbonyl-5-fluorouracil, and then to it is added amine. The reaction proceeds in 1 to 3 hr. It is desirable to add such a dehydrochlorinating agent as triethylamine at this time. If deposited triethylamine hydrochloride is found after the end of the reaction, it is removed by filtration. When the solvent and the like are removed from the filtrate or from the reaction solution of 5- fluorouracil and isocyanate by evaporation under reduced pressure and the residue is stirred in a mixture of hydrochloric acid water and dichloromethane, the object matter is deposited as insoluble crystals and can be collected by filtration, but as the object matter is partly or totally dissolved in dichloromethane, it can be obtained also by drying, concentrating and exsiccating the solution. The product obtained are recrystallized from alcohol, if necessary.

The compounds to be obtained in this manner are, for instance, 1-carbamoyl-5-fluorouracil derivatives containing same of the following N-substituent groups: 2, 3-dimethoxybenzyl, 2, 4-dimethoxybenzyl, 2, 5-dimethoxybenzyl, 2, 6-dimethoxybenzyl, 3, 4-dimethoxybenzyl, 3, 5-dimethoxybenzyl, 2-ethoxy-3-methoxy-benzyl, 3-ethoxy-2-methoxybenzyl, 2, 3-diethoxybenzyl, 2-ethoxy-4-methoxybenzyl, 2-methoxy-4-ethoxybenzyl, 2, 4-diethoxybenzyl, 2-ethoxy-5-methoxybenzyl, 2-methoxy-5-ethoxybenzyl, 2, 5-diethoxybenzyl, 2-ethoxy-6-methoxybenzyl, 2-methoxy-6-ethoxybenzyl, 2, 6-diethoxybenzyl, 3-ethoxy-4-methoxybenzyl, 3-methoxy-4-ethoxybenzyl, 3, 4-diethoxybenzyl, 3-ethoxy-5-methoxybenzyl, 3-methoxy-5-ethoxybenzyl, 3, 5-diethoxybenzyl, 2, 3-dimethoxyphenetyl, 2, 4-dimethoxyphenetyl, 2, 5-dimethoxyphenetyl, 2, 6-dimethoxyphenetyl, 3, 4-dimethoxyphenetyl, 3, 5-dimethoxyphenetyl, 3-ethoxy-4-methoxyphenetyl, 3-methoxy-4-ethoxyphenetyl, 3, 4-diethoxyphenetyl, 2, 3, 4-trimethoxybenzyl, 2, 3, 5-trimethoxybenzyl, 2, 3, 6-trimethoxybenzyl, 2, 4, 5-trimethoxybenzyl, 2, 4, 6-trimethoxybenzyl, 3, 4, 5-trimethoxybenzyl, 2, 3, 4-trimethoxycyclohexyl, 2, 3, 5-trimethoxycyclohexyl, 2, 3, 6-trimethoxycyclohexyl, 2, 4, 5-trimethoxycyclohexyl, 2, 4, 6-trimethoxycyclohexyl, 3, 4, 5-trimethoxycyclohexyl, 2, 3, 4-trimethoxycyclohexylmethyl, 2, 3, 5-trimethoxycyclohexylmethyl, 2, 3, 6-trimethoxycyclohexylmethyl, 3, 4, 5-trimethoxycyclohexylmethyl, 2-ethoxy-4, 5-dimethoxybenzyl, 2, 3, 4-trimethoxycyclohexylethyl, 2, 4, 5-trimethoxycyclohexylmethyl, 2, 4, 5-trimethoxycyclohexylethyl, 2, 4, 6-trimethoxycyclohexylmethyl, 2, 4, 6-trimethoxycyclohexylethyl, 3, 4, 5-trimethoxycyclohexylethyl, 2, 3, 4-trimethoxycyclohexylpropyl, 3, 4, 5-trimethoxyphenylbutyl, 2, 3-dimethoxycyclohexyl, 2,4-dimethoxycyclohexyl, 2,5-dimethoxycyclohexyl, 2, 6-dimethoxycyclohexyl, 3, 4-dimethoxycyclohexyl, 3, 5-dimethoxycyclohexyl, 2-methoxy-3-methylcyclohexyl, 3-methyl-6-methoxycyclohexyl, 2, 3-dimethoxycyclohexylmethyl, 2, 4-dimethoxycyclohexylmethyl, 2, 5-dimethoxycyclohexylmethyl, 2, 6-dimethoxycyclohexylmethyl, 3, 4-dimethoxycyclohexylmethyl, 3-methyl-4-methoxycyclohexylmethyl, 2-methyl-4-methoxycyclohexylethyl, 2-methyl-4-ethoxycyclohexylethyl, 3, 4-dimethoxycyclohexylethyl, 4-ethoxycyclohexyl, 2-methoxycyclohexylmethyl, 2-ethoxycyclohexylmethyl, 3-methoxycyclohexylmethyl, 4-ethoxycyclohexylmethyl, 2-methoxycyclohexylethyl, cyclohexylethyl, 4-methoxycyclohexylethyl, 4-methoxycyclohexylpropyl, cyclohexylpropyl, p-ethoxybenzyl, o-methoxybenzyl, o-ethoxybenzyl, o-methoxyphenetyl, m-methoxybenzyl, p-chlorobenzyl, m-chlorobenzyl, m-chlorophenetyl, 2-chlorocyclohexylethyl, m-bromobenzyl, 4-methoxycyclohexylbutyl, p-methoxyphenylpropyl, p-methoxyphenylbutyl, 1-phenylethyl, 2-phenylpropyl, 1-(p-methoxyphenyl) ethyl, 2-(p-methoxyphenyl) propyl, p-methylthiophenyl, p-methylthiophenylmethyl, p-methoxycarbonylphenyl, p-carboxyphenyl, p-carbamoylphenylmethyl, p-sulfophenylmethyl, p-sulfonamidophenylmethyl, p-acetylaminophenylmethyl, 3-acetylamino-4-methylphenyl, p-methylsulfonylaminophenylmethyl, p-methylsulfonylphenylmethyl, p-cyanophenylmethyl, p-nitrophenylmethyl, 4-(1-(5-fluorouracil) carbonylamino))-cyclohexyl, 1-phenylcyclohexyl, 4-phenylcyclohexylmethyl, 4-methylthiocyclohexyl, 4-acetoxycyclohexyl, 2-acetoxyphenyl, 2-acetoxycyclohexyl, cyclopropyl, 3-cyclohexenyl, cyclopentyl, cyclopentylmethyl, cycloheptyl, 3, 4-methylenedioxycyclohexyl, 3, 4-methylenedioxycyclohexylmethyl, trans-2-phenylcyclopropyl, and 2, 2-dimethyl-3-oxy-4-oxocyclopentyl, etc.

The manufacturing processes for the compounds of this invention will be explained with actual examples in the following.

EXAMPLE 1

To 40 ml of benzene were added 3.92 g (10.02 mol) of homoveratric acid (3, 4-dimethoxyphenylacetic acid), 5.6 g (0.0204 mol) of diphenylphosphoric acid azide and 2.02 g (0.02 mol) of triethylamine in order and the temperature was gradually raised. Foaming was remarkable at 40° C., but the temperature was raised to 80° in 1.5 hr. After cooling, benzene was distilled off under reduced pressure. To the remaining solution was added 2.6 g (0.02 mol) of 5-fluorouracil, and then the solution was heated at 90° C. for 2 hr. To it were added 30 ml of hydrochloric acid water and 30 ml of dichloromethane, and the mixture was stirred. The undissolved portion of 5-fluorouracil was removed by filtration. The dichloromethane layer was separated, stirred with 20 ml of hydrochloric acid water. The solution was filtered when it became turbid and turned white, and 2.92 g of the white crystals of 1-(3, 4-dimethoxybenzylcarbamoyl)-5-fluorouracil (melting point: 127° C.) were collected (Compound No. 1). The remaining dichloromethane layer was evaporated after drying with sodium sulfate and the residue was recrystallized from methanol to obtain 1.26 g of the additional object matter.

EXAMPLE 2

To 4.9 g (0.025 mol) of 2, 5-dimethoxyphenylacetic acid was added 50 ml of benzene, 7.02 g (0.0255 mol) of diphenylphosphoric acid azide and 2.53 g (0.025 mol) of triethylamine in order. The temperature was raised to 80° C. in 2 hr, and then the solution was concentrated under reduced pressure. When 3.25 g (0.025 mol) of 5-fluorouracil was added to the concentrate and heated at 90° C. for 1 hr without isolating the produced isocyanate, the solution became solid as a whole. After cooling, to it were added 300 ml of dichloromethane and 100 ml of hydrochloric acid water. The mixture was entirely stirred, and an insoluble substance produced was collected. The insoluble substance was washed with acid water, recrystallized from methanol and 2.5 g of 1-(2, 5-dimethoxybenzylcarbamoyl)-5-fluorouracil (Compound No. 2, melting point: 185° C.) was obtained (Compound No. 2). The object matter, 1.2 g, was obtained also from the dichloromethane layer. NMR: (CDCl$_3$) 3.8 (3H, S, OCH$_3$) 3.87 (3H, S, OCH$_3$) 4.22 (2H, d, CH$_2$) 6.8 (2H, s, C$_6$H$_2$) 7.36 (1H, s, C$_6$H) 8.25 (1H, d, H of the 6-position) 9.5 (1H, s, NH) 11.8 (1H, s, NH of the 3-position).

EXAMPLE 3

To 40 ml of benzene were added 3.44 g of 3,4-dimethoxyphenylpropionic acid, 5 g of diphenylphosphoric acid azide and 2.1 g of triethylamine and allowed to react as in Example 1, and 1.9 g of 1-(3, 4-dimethoxyphenetylcarbamoyl)-5-fluorouracil (melting point: 151° C.) was obtained (Compound No. 3).

EXAMPLE 4

To 40 ml of benzene were added 3.92 g of 2,4-dimethoxyphenylacetic acid, 5.6 g of diphenylphosphoric acid azide and 2 g of triethylamine and allowed to react as in Example 1 and 3.7 g of 1-(2,4-dimethoxybenzylcarbamoyl)-5-fluorouracil (melting point: 154° C.) was obtained (Compound No. 4).

EXAMPLE 5

5-Fluorouracil, 1.14 g, was dissolved in 30 ml of pyridine, 2.46 g of phosgene was blown into the solution at 5° C., and the solution was allowed to stand at room temperature for 1 hr. Then 1.5 g of 4-ethoxy-3-methoxybenzylamine and 3.2 ml of triethylamine were added to it while cooling with ice, and the solution was stirred at room temperature for 1 hr. Triethylamine hydrochloride was removed from the solution by filtration. The filtrate was concentrated and exsiccated. The residue was dissolved in 100 ml of dichloromethane, and the solution was washed with hydrochloric acid water, dried, concentrated and exsiccated again. The residue was recrystallized from ethanol, and 2.3 g of 1-(4-ethoxy-3-methoxybenzylcarbamoyl)-5-fluorouracil (melting point: 153° C.) was obtained (Compound No. 5). NMR: (DMSOd$_6$) 1.4–1.6 (3H, m, CH$_3$) 3.85 (3H, s, OCH$_3$) 4.04 (2H, q, OCH$_2$) 4.44 (2H, d, CH$_2$) 6.8 (2H, s, C$_6$H$_2$) 7.2 (1H, s, C$_6$H) 8.42 (1H, d, H of the 6-position) 9.2 (1H, m, NH).

EXAMPLE 6

A mixture of 3.9 g of 5-fluorouracil, 6.27 g of 3, 4, 5-trimethoxyphenylisocyanate and 15 ml of pyridine was heated at 90° C. for 2 hr and, after evaporating pyridine, 100 ml of dichloromethane and 200 ml of hydrochloric acid water were added to it. The insoluble substance produced was combined with the substance dissolved in the dichloromethane. The combined substances were washed with water and then with ethanol, and 4.8 g of 1-(3, 4, 5-trimethoxyphenylcarbamoy)-5-fluorouracil (melting point: 168°–170° C.) was obtained (Compound No. 6). NMR: 3.76 (3H s OCH$_3$) 3.84 (6H s OCH$_3$) 6.64–7.0 (2H b C$_6$H$_2$).

EXAMPLE 7

5-Fluorouracil, 3.9 g, was dissolved in 80 ml of pyridine, the solution was cooled to 5° C., and 4 g of phosgene was blown into it. After stirring at 20° C. for 2 hr, the solution was cooled to 5° C., 5.8 g of 2, 3, 4-trimethoxybenzylamine and 3 ml of trimethylamine were gradually added to it, and the temperature was raised to 20° C. in 2 hr. After removing precipitate, pyridine was evaporated from the solution. Hydrochloric acid water and dichloromethane were added to the remainder. The solution was shaken, the dichloromethane layer was evaporated, the residue was recrystallized from methanol, and 4.5 g of 1-(2, 3, 4-trimethoxybenzylcarbamoyl)-5-fluorouracil (melting point: 159° C.) was obtained (Compound No. 7). NMR: 2.74 (6H s CH$_3$) 2.98 (3H s CH$_3$) 4.48 (2H d CH$_2$) 6.7–7.1 (2H m C$_6$H$_2$) 8.42 (H d C$_6$-H) 9.56 (H s NH).

EXAMPLE 8

A mixture of 2.12 g of 2-(3, 4-dimethoxycyclohexyl) ethylisocyanate, 1.5 g of 5-fluorouracil and 50 ml of pyridine was heated at 90° C. for 2 hr. The solution was cooled to 50° C. and pyridine was evaporated under reduced pressure. The residue was shaken in a mixture of 80 ml of dichloromethane and 100 ml of hydrochloric acid water, and the lower layer of the solution was dried and evaporated. The residue was chromatographed on silica gel and 1.65 g of 1-(3, 4-dimethoxycyclohexylethylcarbamoyl)-5-fluorouracil (melting point: 129° C.) was obtained (Compound No. 8). NMR: 0.73–2.27 (9H b CH$_2$) 2.77–3.40 (2H b C$\underline{H}_2$—NH) 3.30–3.57 (H b C$\underline{H}$OCH$_3$) 3.35 (6H s OCH$_3$) 3.50–3.77 (H b CHOC$\underline{H}_3$) 8.42 (H d C$_6$—H) 9.20 (H b N$\underline{H}$ CO).

EXAMPLE 9

Cyclopentylisocyanate, 5.67 g, was allowed to react with 5-fluorouracil, 4.6 g, in 17 g of pyridine at 90° C. for 2 hr, then the pyridine was evaporated and the residue was shaken with 100 ml of dichloromethane and 100 ml of hydrochloric acid water. The lower layer of the mixture was dried and exsiccated. The residue was recrystallized from ethanol and 8.3 g of 1-cyclopentylcarbamoyl-5-fluorouracil (melting point: 137° C.) was obtained (Compound No. 9) was obtained. NMR: 1.00–2.28 (6H b CH) 3.56–4.12 (1H b C$\underline{H}$—NHCO) 8.40 (1H d C$_6$—H) 8.68–9.08 (1H b N$\underline{H}\overline{C}$O) 9.48 (1H b N$_3$—H).

EXAMPLE 10

The 2, 4-dimethoxycyclohexylamine reduced from 2, 4-dimethoxyaniline by hydrogen at 110 atmospheres over a ruthenium oxide catalyst in methanol was treated with phosgene and 2, 4-dimethoxycyclohexylisocyanate was synthesized. This isocyanate, 9.2 g, was allowed to react with 6.8 g of 5-fluorouracil in 30 ml of pyridine at 90° C. for 2 hr. After evaporating the pyridine, the residue was chromatographed on silica gel and two kinds of isomers, 3.2 and 2.8 g respectively, of 1-(2, 4-dimethoxycyclohexylcarbamoyl)-5-fluorouracil were obtained. Their melting points were 122°–125° C. (Compound No. 10) and 128°–130° C. (Compound No. 11), respectively. NMR: 0.7–2.50 (6H b CH$_2$) 2.65 (H s NHC$\underline{H}$) 3.58 (6H s OCH$_3$) 4.10–4.51 (H s C$\underline{H}$OCH$_3$) 8.38 ($\overline{H}$ d C$_6$—H) 9.50 (H d N$\underline{H}$CO) 12.25 (H b $\overline{N}_3$—H).

EXAMPLE 11

The kinds of 1-carbamoyl-5-fluorouracil derivatives which we have obtained proceeding as in Example 8 are shown in Table 1. The products are variable according to the kind of isocyanate combined with 5-fluorouracil. In table 1 the yield, melting point and NMR of the compounds obtained are given.

TABLE 1

| Compound No. | $-(CH_2)_m(CH_n)-A-\begin{smallmatrix}R^2\\R^1\phantom{xx}R^3\\R^4\end{smallmatrix}$ | Yield (%) | Melting point (°C.) | NMR |
|---|---|---|---|---|
| 12 | -CH₂CH₂- (2,3,4-trimethoxyphenyl: OCH₃, OCH₃, OCH₃) | 68.0 | 138 | 2.75(2H t CH₂) 3.78(2H t CH₂NH) 3.78(6H s OCH₃) 3.82(3H s CH₃) 6.60(2H q C₆H₂) 8.35(H d C₆—H) 8.92(H s NH) |
| 13 | -CH₂- (2,4,5-trimethoxyphenyl: OCH₃, OCH₃, OCH₃) | 44.0 | 165 | 3.68(3H s OCH₃) 3.77(3H s OCH₃) 3.79(3H s OCH₃) 4.35(2H d CH₂NHCO) 6.61(H s C₆H) 6.83(H s C₆H) 8.30(H d C₆—H) 9.43(H t NHCO) 12.16(H b N₃—H) |
| 14 | -CH₂- (3,4,5-trimethoxyphenyl: CH₃O, OCH₃, OCH₃) | 73.0 | 166 | 3.80(9H s OCH₃) 4.50(2H d CH₂NHCO) 7.52–7.68(2H bs C₆H₂) 8.36(H d C₆—H) 9.32(H b NHCO) |
| 15 | (2,4,6-trimethylcyclohexyl: CH₃, CH₃, CH₃) | 64.0 | 145 | 0.40–1.00(7H b CH₂) 0.89(9H d CH₃) 3.54–4.60(H b CHNHCO) 8.50(H d C₆—H) 9.03(H d NHCO) |
| 16 | (3,3,5-trimethylcyclohexyl: CH₃, CH₃, CH₃, CH₃) | 35.0 | 153 | 0.32–2.12(16H b CH₂) 3.76(H b CHNHCO) 8.32(H d C₆—H) 8.88(H b NHCO) |

TABLE 1-continued

| Compound No. | $-(CH_2)_m(CH)_n-A\genfrac{}{}{0pt}{}{R^2}{R^4}\genfrac{}{}{0pt}{}{}{R^3}$ with $R^1$ | Yield (%) | Melting point (°C.) | NMR |
|---|---|---|---|---|
| 17 | cyclohexyl with CH₃, OCH₃, OCH₃ | 73.0 | 171 | 1.13–2.35(6H b CH₂) 3.00–3.56(2H b CH—O) 3.30(3H s OCH₃) 3.35(3H s OCH₃) 3.60–4.32(H m CHNH) 8.45(H d C₆—H) 9.65(H d NHCO) 12.2(Hb NH) |
| 18 | cyclohexyl with CH₃, CH₃, OCH₃ | 55.2 | 162 | 0.56–2.20(6H b CH₂) 0.88(3H d CH₃) 3.30–4.00(2H b CHNHCO, CHOCH₃) 3.56 (3H s OCH₃) 8.33(H d C₆—H) 9.38(H b NHCO) 12.25(H b N₃—H) |
| 19 | cyclohexyl with CH₃, OCH₃, OCH₃ | 60.1 | 164 | 0.90–1.93(6H b CH₂) 3.33(3H s OCH₃) 3.42(3H s OCH₃) 3.40–3.63(H m CHNH) 3.63–4.16(2H m CHOCH₃) 8.35(H d C₆—H) 9.65(H d NHCO) |
| 20 | —CH₂— cyclohexyl with OCH₃ | 68.4 | 142–144 | 1.00–2.30(9H b CH₂, CH) 3.23–3.67(3H b CHOCH₃, CHNHCO) 3.35(3H s OCH₃) 8.50 (H d C₆—H) 9.23(H b NHCO) |
| 21 | —CH₂— cyclohexyl with OC₂H₅ | 58.0 | 130–132 | 1.20(3H t OCH₂CH₃) 0.87–2.20(9H b CH) 3.00–4.53(5H m CH—OC₂H₅ O—CH₂—CH₃ CH₂—NHCO) 8.55(1H d C₆H) 9.19(H b NHCO) |
| 22 | —CH₂— cyclohexyl with OCH₃ | 23.0 | 108–109 | 0.6–2.36(8H b CH) 2.88–3.68(3H b CHOCH₃, CH₂NHCO) 3.28(3H s OCH₃) 8.36(1H d C₆H) 9.04(1H b NHCO) |

TABLE 1-continued

| Compound No. | $-(CH_2)_m(CH)_n-A \begin{matrix} R^2 \\ \| \\ R^1 \end{matrix} \begin{matrix} R^3 \\ R^4 \end{matrix}$ | | Yield (%) | Melting point (°C.) | NMR |
|---|---|---|---|---|---|
| 23 | | | 25.0 | 109–110 | 0.62–2.56(9H b CH) 2.96–3.36(2H b CH$_2$NHCO) 3.28(3H s OCH$_3$) 3.36–3.68(1H b CH—OCH$_3$) 7.28–7.84(1H b N$_3$—H) 8.42(1H d C$_6$H) 9.04(1H b NHCO) |
| 24 | —CH$_2$CH$_2$— | cyclohexyl-OCH$_3$ | 56.0 | 128–130 | 0.80–2.07(11H b CH) 2.93–3.67(3H m CHOCH$_3$ CH$_2$NHCO) 3.30(3H s OCH$_3$) 8.47(1H d C$_6$H) 8.95(1H b NHCO) |
| 25 | —(CH$_2$)$_2$— | cyclohexyl | 73.2 | 139 | 0.70–2.07(13H b CH) 3.43(2H dt CH$_2$—NHCO) 8.47(1H d C$_6$—H) 9.04(1H b NH—CO) 9.97(1H b N$_3$H) |
| 26 | —(CH$_2$)$_3$— | cyclohexyl-OCH$_3$ | 65.2 | 110 | 0.60–2.30(13H b CH) 2.77–3.60(3H m CH—OCH$_3$ CH—NHCO) 3.28(3H s OCH$_3$) 8.47(1H d C$_6$—H) 8.97(1H b NH—CO) |
| 27 | —(CH$_2$)$_3$— | cyclohexyl | 60.2 | 133 | 0.62–2.30(15H b CH) 2.95–3.80(2H b CHNHCO) 8.40(1H d C$_6$—H) 9.20(1H b NHCO) 12.36(1H b N$_3$—H) |
| 28 | —CH$_2$— | phenyl-OC$_2$H$_5$ | 55.1 | 159 | 1.40(3H d CH$_2$CH$_3$) 4.30(2H q CH$_2$CH$_3$) 4.66(2H d CH$_2$—NHCO) 7.10–7.43(4H m H—C$\begin{matrix}C\\C\end{matrix}$) 8.53(1H d C$_6$—H) 9.30(2H NHCO N$_3$—H) |
| 29 | —CH$_2$— | phenyl-OCH$_3$ | 69.1 | 154 | 3.82(2H/2 s OCH$_3$) 3.84(3H/2 s OCH$_3$) 4.20(2H/2 s CH$_2$Ph) 4.44(2H/2 d CH$_2$Ph) 6.04 (H/2 b NHCO) 6.56–6.96(2H m C$_6$H$_2$) 7.18(2H m C$_6$H$_2$) 8.32(1H d C$_6$—H) 9.52(H/2 b NH CO) 12.20(H b N$_3$—H) |

TABLE 1-continued

| Compound No. | $-(CH_2)_m(CH)_n-A\begin{matrix}R^2\\R^3\\R^4\end{matrix}$ with $R^1$ | Yield (%) | Melting point (°C.) | NMR |
|---|---|---|---|---|
| 30 | $-CH_2-$ (phenyl with $OC_2H_5$ ortho) | 55.2 | 146–148 | 1.13(3H/2 t OCH$_2$CH$_3$) 1.26(3H/2 t OCH$_2$CH$_3$) 3.94(2H/2 q OCH$_2$CH$_3$) 4.07(2H/2 q OCH$_2$CH$_3$) 5.22(H/2 b NHCO) 6.60–7.00(2H m C$_6$H$_2$) 7.00–7.44(2H m C$_6$H$_2$) 8.40(H d C$_6$—H) 9.50(H/2 b NHCO) |
| 31 | $-(CH_2)_2-$ (phenyl with $OCH_3$ ortho) | 72.3 | 166 | 2.80(2H t CH$_2$—CH$_2$—NH) 3.20–3.60(2H m CH$_2$—CH$_2$—NH) 3.78(3H s OCH$_3$) 6.80–7.20(4H m C$_6$H$_4$) 8.13(1H d C$_6$H) 9.08(1H b NH—CO) 12.46(1H b N$_3$—H) |
| 32 | $-CH_2-$ (phenyl with $OCH_3$ meta) | 75.2 | 149 | 3.83(3H s OCH$_3$) 4.32(2H d CH$_2$—Ph) 6.95(2H s Ph) 7.20(2H m Ph) 8.32(1H d C$_6$—H) 9.58(1H b NHCO) 12.25(1H b N$_3$—H) |
| 33 | $-CH_2-$ (phenyl with Cl para) | 69.2 | 156 | 4.58(2H d CH$_2$—NHCO) 7.32(4H s Ph) 8.37(1H d C$_6$—H) 9.64(1H b NHCO) 12.36(1H b N$_3$—H) |
| 34 | $-CH_2-$ (phenyl with Cl meta) | 61.2 | 155 | 4.52(2H d CH$_2$—Ph) 7.30(2H s Ph) 7.63(2H s Ph) 7.36(2H d C$_6$—H) |
| 35 | $-CH_2-$ (phenyl with Cl ortho) | 55.2 | 166 | 4.62(2H d CH$_2$NHCO) 7.80–7.60(4H b Ph) 8.34(1H d C$_6$—H) 9.68(1H b NHCO) 12.32(1H b N$_3$—H) |

TABLE 1-continued

| Compound No. | $-(CH_2)_m(CH)_n-A\begin{matrix}R^1\\|\\\phantom{-}\end{matrix}\begin{matrix}R^2\\R^3\\R^4\end{matrix}$ | Yield (%) | Melting point (°C.) | NMR |
|---|---|---|---|---|
| 36 | $-(CH_2)_2-$ [3-chlorophenyl] | 71.1 | 155 | 2.88(2H t CH$_2$—Ph) 3.61(2H dt CH$_2$NHCO) 7.00-7.28(4H m Ph) 8.33(1H d C$_6$—H) 9.20(1H b NHCO) |
| 37 | $-(CH_2)_2-$ [2-chlorophenyl] | 62.1 | 155 | 3.03(2H t CH$_2$—CH$_2$—NH) 3.55(2H dd CH$_2$CH$_2$NH) 7.00-7.56(4H m Ph) 8.35(1H d C$_6$—H) 9.60(1H b NHCO) |
| 38 | $-CH_2-$ [3-bromophenyl] | 66.6 | 138 | 4.47(2H dd CH$_2$NHCO) 7.27(1H s Ph) 7.30(1H s Ph) 7.50(1H s Ph) 7.67(1H s Ph) 8.35(1H d C$_6$—H) 9.65(1H b CHNHCO) |
| 39 | cyclohexenyl | 70.1 | 140-141 | 1.43-2.87(6H b CH) 3.70-4.47(1H b CHNHCO) 5.67(1H s HC$\begin{matrix}C\\\|\\C\end{matrix}$) 5.70(1H s HC$\begin{matrix}C\\\|\\C\end{matrix}$) 8.44(1H d C$_6$—H) 9.47(1H d NHCO) 12.00(1H b N$_3$—H) |
| 40 | $-CH_2-$ cyclopentyl | 50.5 | 161 | 0.80-2.24(7H m CH) 3.28(2H dd CH$_2$NHCO) 8.36(1H d C$_6$—H) 8.80(1H s NHCO) |
| 41 | $\begin{matrix}CH_3\\\|\\-CH-\end{matrix}$ phenyl | 62.2 | 116-118 | 1.56(3H d CH—CH$_3$) 5.04(1H dq CH—CH$_3$) 7.24(5H s HC$\begin{matrix}C\\\|\\C\end{matrix}$) 8.36(1H d C$_6$—H) 9.42(1H d NHCO) |
| 42 | cyclopropyl-C$_6$H$_5$ | 39.2 | 175-176 | 1.30(2H dd CH$_2$) 2.16(1H b CH) 2.96(1H b CH) 7.20(5H s Ph) 8.33(1H d C$_6$—H) 9.36(1H b NHCO) 12.24(1H b N$_3$—H) |

TABLE 1-continued

| Compound No. | —(CH₂)ₘ(CH)ₙ—A—R³ / R¹, R², R⁴ | Yield (%) | Melting point (°C.) | NMR |
|---|---|---|---|---|
| 43 | R¹=C₂H₅, R²=—CH—C₆H₅ | 66.2 | 154–156 | 0.92(3H t CH₂—CH₃) 4.75(1H dt CHNHCO) 7.09(5H s Ph) 8.25(1H d C₆—H) 9.33(1H d NHCO) |
| 44 | ![structure with NHCO—N, N—H, C=O, F] | 29.1 | >275 | 0.88–2.28(8H m CH₂) 3.30(2H m NHCH) 8.40(2H d C₆—H) 10.56 11.20 12.32 (2H b N₃—H) |
| 45 | cyclohexyl— | 53.2 | 133–134 | 1.20(3H t OCH₂CH₃) 1.00–2.12 (8H b CH₂CH₂) 3.20–3.60(1H b CHNH) 3.46(2H q O—CH₂CH₃) 3.72(1H t CH—O—Et) 8.32(1H d C₆—H) 8.88(1H b NHCO) 9.36(1H b N₃—H) (—CO—) |
| 46 | —CH₂—(cyclohexyl)—OC₂H₅ | 54.1 | 113–115 | 0.60–2.20(9H bm CH₂CH₃) 1.17(3H t OCH₂CH₃) 3.26(1H b CHO—Et) 3.26(1H dd CH—NHCO) 3.44(2H q OCH₂CH₃) 8.45(1H d C₆—H) 9.06(1H bt NHCO) 10.10(1H b N₃—H) |
| 47 | —CH₂—(cyclohexyl)—OC₂H₅ | 14.3 | 137–138 | 0.70–2.30(9H bm CH₂CH₂) 1.14(3H t OCH₂CH₃) 3.16(1H b CHO—Et) 3.24(1H dd CH—NHCO) 3.50(2H q OCH₂CH₃) 8.40(1H d C₆—H) 9.04(1H b NHCO) 9.68(1H b N₃—H) |
| 48 | —(CH₂)₂—(cyclohexyl)—OCH₃ | 6.3 | 133–134 | 0.80–2.30(11H bm CH₂CH₂) 3.10(1H b CH—OCH₃) 3.34(3H s OCH₃) 3.42(2H b CHNHCO) 8.43(1H d C₆—H) 8.94(1H b NHCO) |
| 49 | —(CH₂)₂—(cyclohexyl)—OCH₃ | 30.2 | 126–127 | 1.08–2.04(11H b CH₂CH₂) 3.28(3H s OCH₃) 3.40(3H b CHNHCO CH—OCH₃) 8.44(1H d C₆—H) 8.96(1H b NHCO) |

Yields combined: {54.1, 14.3} = 68.4; {6.3, 30.2} = 36.5

TABLE 1-continued

| Compound No. | $-(CH_2)_m(CH)_n-A\begin{smallmatrix}R^2\\\|\\-R^3\\R^4\end{smallmatrix}$ with $R^1$ | Yield (%) | Melting point (°C.) | NMR |
|---|---|---|---|---|
| 50 | —CH₂— cyclohexyl with OCH₃, OCH₃, OCH₃ substituents | 46.2 | 98–100 | 0.78–2.25(7H bm CH₂CH) 2.84–3.84(3H bm CH₂NHCO CH—OCH₃) 3.55(3H s OCH₃) 3.50(3H s OCH₃) 4.12(1H b CH—OCH₃) 8.43(1H d C₆—H) 9.15(1H b NHCO) |
| 51 | —CH₂— cyclohexyl with OCH₃, OCH₃, OCH₃ substituents | 15.4 | 130–132 | 1.04–2.50(7H bm CH₂CH) 3.04–3.70(4H b CH—OCH₃ CH—NHCO) 8.43(1H d C₆—H) 9.20(1H NHCO) |
| 52 | —CH₂— cyclohexyl with OCH₃, OCH₃, OCH₃ substituents | 27.8 | 125–127 | 0.96–1.34(2H m CH₂CH) 1.66(2H b CH₂CH₂) 2.12(2H b CH₂CH₂) 2.80–3.60(4H CH—OCH₃ CH₂NHCO) 3.32(3H s OCH₃) 3.40(3H s OCH₃) 8.40(1H d C₆—H) 9.32(1H b NHCO) |
| 53 | —CH₂— cyclohexyl with OCH₃, OCH₃ substituents | 34.5 | 165–166 | 1.36(6H bm CH₂CH₂) 3.00–3.72(2H b CH—OCH₃) 3.40(3H s OCH₃) 3.42(3H s OCH₃) 3.92(1H b CHNHCO) 8.40(1H d C₆—H) 9.36(1H b NHCO) |
| 54 | —CH₂— cyclohexyl with OCH₃, OCH₃ substituents | 56.2 | 41–42 | 1.00–2.28(7H m CH₂CH₂) 3.00–3.96(4H bm CH—OCH₃ CH₂—NHCO) 3.16(6H s OCH₃) 8.41(1H d C₆—H) 9.08(1H b NHCO) |
| 55 | —CH₂— cyclohexyl with OCH₃, OC₂H₅ substituents | 37.4 | 38–41 | 0.72–1.24(7H m CH₂CH₂) 1.20(3H t OCH₂CH₃) 2.96–3.86(4H CH—OCH₃ CH—OEt CH₂NHCO) 3.27(3H s OCH₃) 7.51, 8.21(1H d C₆—H) 9.09(1H b NHCO) |

TABLE 1-continued

| Compound No. | $-(CH_2)_m(CH)_n-A$ with $R^1$, $R^2$ / $R^3$, $R^4$ | Yield (%) | Melting point (°C.) | NMR |
|---|---|---|---|---|
| 56 | $-CH_2CH_2-$ ; cyclohexyl with three OCH₃ groups | 78.6 | 139–140 | 1.08–2.12(4H bm CH₂CH₂) 3.16(2H b CH₂NHCO) 3.34(6H s OCH₃) 3.58(3H s OCH₃) 3.80(1H b CH—OCH₃) 3.94(1H b CH—OCH₃) 4.42(1H b CH—OCH₃) 8.37(1H d C₆—H) 10.05(1H d NHCO) |
| 57 | cyclohexyl with OCH₃, OCH₃, OCH₃, CH₃ | 61.2 | 149–151 | 0.77–2.21(4H m CH₂CH₂) 3.01–4.21(4H m CH—OCH₃, CH—NHCO) 3.40(6H s OCH₃) 3.60(3H s OCH₃) 8.37(1H d C₆—H) 9.15(1H d NHCO) |
| 58 | cyclohexyl with OCH₃, OCH₃, OCH₃, CH₃ | 62.2 | 126 | 1.12–2.30(7H m CH₂CH₂) 2.96–3.92(5H m CH—OCH₃, CH₂—NHCO) 3.40(3H s O—CH₃) 3.45(3H s O—CH₃) 3.53(3H s O—CH₃) 8.45(1H d C₆—H) 8.98(1H b NHCO) 9.72(1H b N₃—H) |
| 59 | $C_2H_5$—CH—cyclohexyl | 82.1 | 117–118 | 0.88(3H t CH₂CH₃) 1.16(4H b CH₂CH₂) 1.68(9H b CH₂CH₂) 3.80(1H b CH—NHCO) 8.22(1H d C₆—H) 8.88(1H b NHCO) |
| 60 | H, C₆H₅ (R) / CH₃ | 46.7 | 127–129 | 1.56(3H d CH—CH₃) 5.04(1H dq CH—NHCO) 7.24(5H s Ph) 8.36(1H d C₆—H) 9.42(1H d NHCO) |
| 61 | H, cyclohexyl (R) / CH₃ | 56.2 | 118–119 | 0.90–1.48(5H m CH₂CH₂) 1.19(3H d CH—CH₃) 1.76(6H b CH₂CH₂) 8.44(1H d C₆—H) 8.96(1H d NHCO) 9.62(1H b N₃—H) |

TABLE 1-continued

| Compound No. | $-(CH_2)_m(CH)_n-A\begin{matrix}R^2\\R^1\end{matrix}\begin{matrix}R^3\\R^4\end{matrix}$ | Yield (%) | Melting point (°C.) | NMR |
|---|---|---|---|---|
| 62 | $CH_3$, CH, H, cyclohexyl (S) | 38.3 | 116–117 | 0.90–1.48(5H m $CH_2CH_2$) 1.19(3H d CH—$CH_3$) 1.76(6H b $CH_2CH_2$) 8.44(1H d $C_6$—H) 8.96(1H d NHCO) 9.62(1H b $N_3$—H) |
| 63 | $-CH_2-$ cyclohexyl with $CH(CH_3)_2$ | 27.5 | 93–96 | 0.64–1.40(9H bm $CH_3$) 1.00–2.20(8H b $CH_2CH_2$) 4.16(1H b CHNHCO) 8.54(1H d $C_6$—H) 9.18(1H b NHCO) |
| 64 | cyclohexyl with three $OCH_3$ groups | 32.6 | 150–152 | 0.72–2.36(4H bm $CH_3$) 3.17(2H m NHCH $CHOCH_3$) 3.37(3H s $OCH_3$) 3.39(3H s $OCH_3$) 3.43(3H s $OCH_3$) 3.62(1H m $CHOCH_3$) 4.44(1H m $CHOCH_3$) 8.38(1H d $C_6$—H) 9.72(1H d NHCO) |

The compounds of this investigation were examined for their carcinostatic activity. The results of examinations are shown by examples in the following.

EXAMPLE 1

Experimental animals (BDF$_1$ mice) were divided into 2 groups, test and control, of 6 individuals each, and 10 Lewis Lung carcinoma cells were implanted intraperitoneally each animal. Each of the test compounds was suspended in 0.5% CMC solution and a fixed amount of the suspension was orally given to each animal of the test group 3 times a week continuously. The Increase of Life Span in the test group was calculated by the following formula:

$$\text{Increase of Life Span } (ILS\ \%) = \frac{T - C}{C} \times 100$$

wherein
T: the number of days before death in the test group,
C: the number of days before death in the control group.

When 58 kinds of compounds, No. 6–64, were examined at doses of 50 and 100 mg as mentioned above, the ILS obtained was not less than 10 and not less than 30, respectively, in every compound examined.

EXAMPLE 2

The ILS % of mice was examined in the same manner as in Example 1 with 5 kinds of compounds (Compound No. 1 to 5) at the same time as compared with those of 2 kinds of compounds in the public domain 1-(4-methoxybenzylcarbamoyl)-5-fluorouracil (Control 1) and 1-(4-ethoxycarbonyl-benzylcarbamoyl)-5-fluorouracil (Control 2). The results obtained are given in Table 2.

TABLE 2

| | Increasing rate of the days of survival (%) | | |
|---|---|---|---|
| | Dose mg/kg | | |
| | 50 | 100 | 200 |
| Compound No. | | | |
| 1 | 14 | 62 | 105 |
| 2 | 38 | 71 | 81 |
| 3 | 16 | 40 | 80 |
| 4 | 15 | 38 | 62 |
| 5 | 12 | 50 | 85 |
| Control | | | |
| 1 | 10 | 28 | 24 |
| 2 | 9 | 12 | −4 |

The carcinostatic agents of this invention can be used as preparations for oral administration, that is, capsules, tablets, granules and syrups, and as preparations for parenteral use, that is, injections, suppositories and ointments. They may be manufactured by using the methods and vehicles which are patent to the public. A daily dose for an adult is 100–700 mg, and desirably 300–500 mg.

Two examples of the preparations of this invention are shown in the following.

EXAMPLE 1

A mixture of 100 mg of Compound No. 1, 100 mg of Compound No. 53, 50 mg of lactose, 50 mg of potato starch and 10 mg of crystalline cellulose were contained in a gelatin capsule. Three capsules per day are administered in divided doses after meals.

EXAMPLE 2

After Witepsol w 35, 500 g, was heated to 60° C., 100 g of Compound No. 2 and 100 g of Compound No. 8 were added to it little by little, and homogenized. The mixture was cooled to 40° C. and filled up into a plastic container with a suppository filling machine and then was cooled to 15° C. A daily dose is about 300–600 mg.

We claim:
1. A 1-(N-substituted carbamoyl)-5-fluorouracil derivative having the formula:

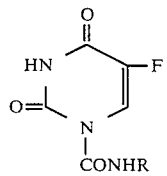

wherein R is a 4-alkoxycyclohexyl group-containing radical selected from the group consisting of 2,3,4-trimethoxycyclohexylethyl, 2,3,4-trimethoxycyclohexyl, 2,4-dimethoxycyclohexylmethyl, 3,4-dimethoxycyclohexylethyl, 2,4-dimethoxycyclohexyl, 2,4,5-trimethoxycyclohexyl, 3,4-dimethoxycyclohexylmethyl, 3,4,5-trimethoxycyclohexyl, 4-ethoxycyclohexyl and 4-ethoxycyclohexylmethyl.

2. A carcinostatic agent comprising therapeutically effective amount of a compound as claimed in claim 1 together with at least one pharmaceutically-acceptable, substantially nontoxic common auxiliary and/or additive substance.

3. 1-(2,3,4-trimethoxycyclohexylethylcarbamoyl)-5-fluorouracil.
4. 1-(2,3,4-trimethoxycyclohexylcarbamoyl)-5-fluorouracil.
5. 1-(2,4-dimethoxycyclohexylmethylcarbamoyl)-5-fluorouracil.
6. 1-(3,4-dimethoxycyclohexylethylcarbamoyl)-5-fluorouracil.
7. 1-(2,4-dimethoxycyclohexylcarbamoyl)-5-fluorouracil.
8. 1-(2,4,5-trimethoxycyclohexylcarbamoyl)-5-fluorouracil.
9. 1-(3,4-dimethoxycyclohexylmethylcarbamoyl)-5-fluorouracil.
10. 1-(3,4,5-trimethoxycyclohexylcarbamoyl)-5-fluorouracil.
11. 1-(4-ethoxycyclohexylcarbamoyl)-5-fluorouracil.
12. 1-(4-ethoxycyclohexylmethylcarbamoyl)-5-fluorouracil.

* * * * *